United States Patent [19]

Silber

[11] Patent Number: 4,526,166

[45] Date of Patent: Jul. 2, 1985

[54] DISCONNECTIBLE SECTION BANDAGE

[76] Inventor: Arthur L. Silber, 1425 Rodeo Rd., Arcadia, Calif. 91006

[21] Appl. No.: 522,789

[22] Filed: Aug. 12, 1983

[51] Int. Cl.³ .............................................. A61L 15/00
[52] U.S. Cl. .................................................. 128/156
[58] Field of Search ................................ 128/155, 156

[56] References Cited

U.S. PATENT DOCUMENTS

| | | | |
|---|---|---|---|
| 2,834,347 | 5/1958 | Connally | 604/389 |
| 3,163,162 | 12/1964 | Basseches | 128/156 |
| 3,528,426 | 9/1970 | Vukojevic | 128/155 |
| 3,885,559 | 5/1975 | Economou | 128/156 |
| 3,927,669 | 12/1975 | Glatt | 128/156 |
| 4,334,530 | 6/1982 | Hassell | 128/156 |

Primary Examiner—C. Fred Rosenbaum
Assistant Examiner—Harrie R. Samaras
Attorney, Agent, or Firm—William W. Haefliger

[57] ABSTRACT

A bandage includes first and second carrier strips, the first strip carrying a liquid absorbent, soft, pad of material which is to be placed over a wound. The second strip carries an adhesive to be placed onto the patient's skin at a location spaced from the wound. The two strips have ends which are connected by a releasable attachment forming a third element such as a tear string which is easily manipulable to free the strips from one another. This enables lifting of the pad and first strip independently of the second strip, so that force applied to the second strip to free it from the skin is not transferable to the first strip and wound.

7 Claims, 5 Drawing Figures

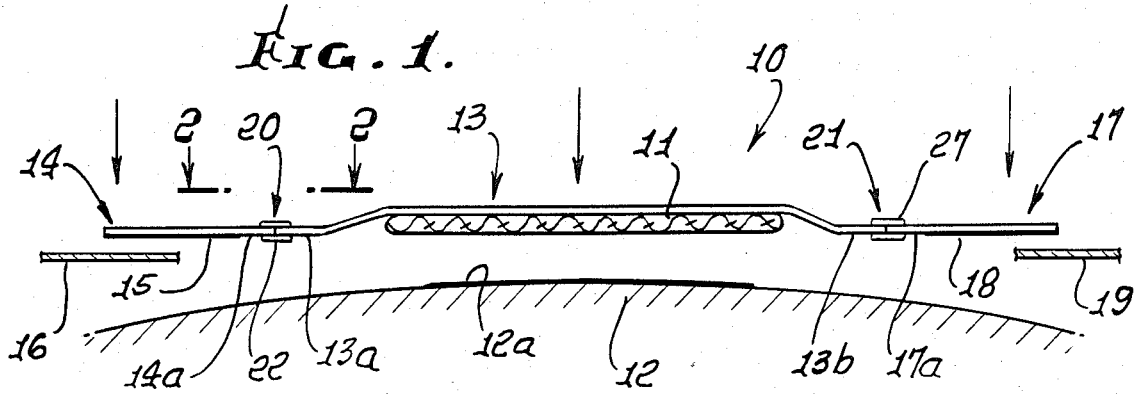
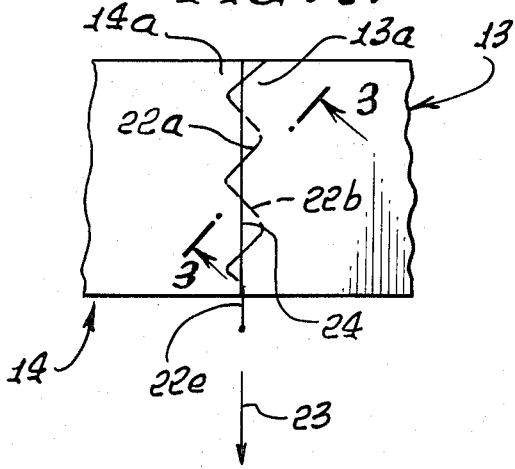
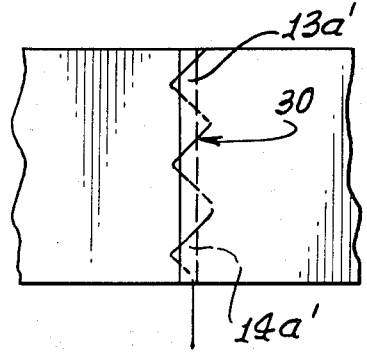
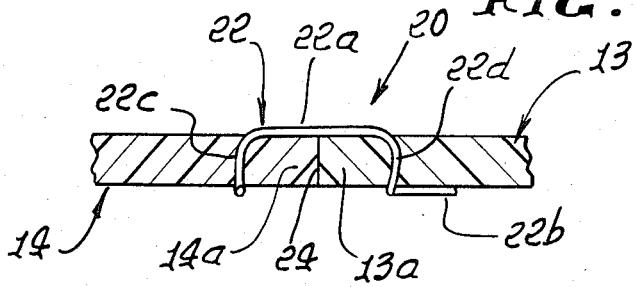
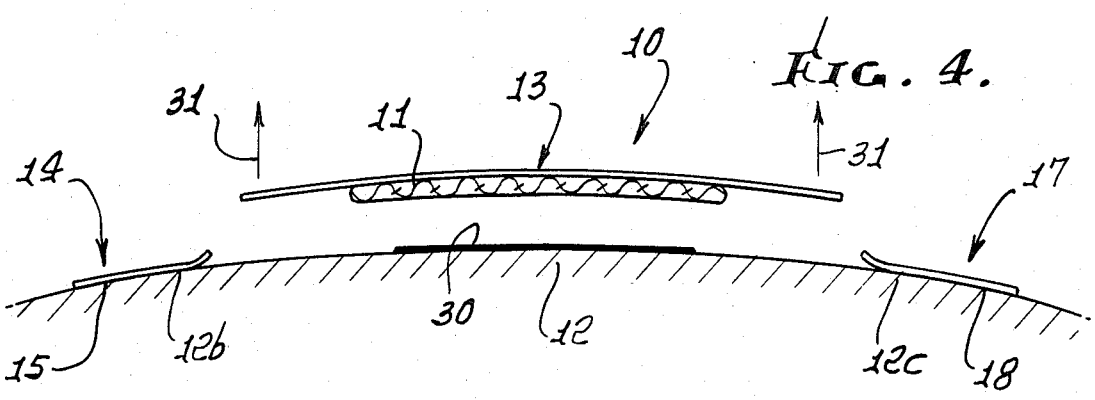

DISCONNECTIBLE SECTION BANDAGE

BACKGROUND OF THE INVENTION

This invention relates generally to bandages, and more specifically to improvements in bandages which are less uncomfortable and cumbersome in their use and removal from painful and healing skin areas.

Bandages such as Band-aids are highly useful; however, they are frequently difficult to remove without injury to a not yet healed wound area. This results from the fact that pulling the end portion of the bandage carrying adhesive to free it from skin area oftentimes transmits sideways pull to the pad adherent to the wound or scab area, thus inadvertently injuring healing of the wound, burns, etc. This is uncomfortable and damaging.

SUMMARY OF THE INVENTION

It is a major object of the invention to provide an improved bandage overcoming the above described disadvantages and problems, as well as others, as will appear. Basically, the improved bandage concerns a disconnectible section bandage. It typically comprises:

(a) a liquid absorbent, soft, pad of material adapted to be placed over a wound, (b) a first strip carrying said material, (c) a second strip carrying an adhesive adapted to be pressed onto one skin area spaced from the wound, and (d) a primary releasable attachment interconnecting said first and second strips and adapted to be manipulated to free the connection therebetween.

As will appear the attachment may advantageously comprise a string adapted to be pull-displaced, and may be stitched to the ends of the first and second strips in such a manner as to be easily so displaced to free the two sections. Thereafter, removal of the adhesive coated strip cannot transfer pull to the first strip which supports the pad, and the latter may be independently and carefully lifted from the wound area without restriction imposed by the adhesive coated strip. Two such strings may be employed, to respectively releasably connect the ends of the pad carrying middle strip to two adhesive carrying strips, whereby the latter may both be easily disconnected prior to pulling them free of the skin area.

These and other objects and advantages of the invention, as well as the details of an illustrative embodiment, will be more fully understood from the following description and drawings, in which:

DRAWING DESCRIPTION

FIG. 1 is a side elevation of a bandage incorporating the invention, during application thereof;

FIG. 2 is a plan view on lines 2—2 of FIG. 1;

FIG. 3 is an enlarged section on lines 3—3 of FIG. 2;

FIG. 4 is a view like FIG. 1 but showing stepwise removal of the bandage from a wound; and FIG. 5 is a view like FIG. 2, but showing a modification.

DETAILED DESCRIPTION

In FIGS. 1-3, a disconnectible section bandage 10 includes soft, liquid absorbent pad of material 11 adapted to be placed directly over and upon a wounded or sore skin area 12a on a user's body 12. The material 11 may consist of open work, porous, natural or synthetic fibrous material, one example being gauze. The pad frequently tends to adhere to the wound, over time. It is carried at the underside of a first thin strip 13 of support material, one example being polyethylene or other synthetic resinous film. That strip has opposite end portions 13a and 13b.

A second strip 14, usually of the same width as strip 13, has one end portion 14a extending in end-adjacent relation to the strip end 13a; thus, for example, the end portions 13a and 14a may abut, or nearly abut one another, as shown. Strip 14 conventionally carries a thin layer of adhesive 15 at its underside, which is exposed when a protective flap 16 is peeled away from the underside of strip and from about one-half the underside of pad 11. Stick-on adhesive 15 may consist of conventional material. In the same manner, a third strip 17 may be provided, with one end portion 17a extending in end-adjacent relation to strip end 13b (as for example end-abutting relation). Strip 17 also carries a thin layer of adhesive 18 at its underside, corresponding to adhesive layer 15. See also protective flap 19 which is peeled away to expose the adhesive, and the other one-half of pad 11.

In accordance with the invention, a primary releasable attachment 20 interconnects the first and second strips 13 and 14, as at their end portions 13a and 14a, and is characterized as adapted to be manipulated, for example pull-displaced, to free the interconnection of such end portions. This disconnection of the strips is effected at such time the bandage is to be removed, so that strip 14 may be forcibly pulled to free the adhesive 15 from the skin area 12b (see FIG. 4), without disturbing the pad supported section or strip 13. The latter may then be carefully lifted free of the wound (or alternatively before strip 14 is forcibly pulled free). The same type attachment 21 connects the first and third strips 13 and 17, as at their end portions 13b and 17a. After manipulation of connection 21, the central section or strip 13 is completely free to be carefully lifted from the wound, without being affected or pulled endwise during pull-displacement of either of strips 14 and 17 to free the adhesives from the skin areas 12b and 12c. See FIG. 4, and lifting of pad 11 completely away from the wound and healed material 30, arrows 31 indicating such lifting.

Referring now to FIGS. 2 and 3, the connection 20 comprises a string, such as a thread 22, adapted to be endwise pull-displaced, transversely of the lengthwise extent of the bandage 10, i.e. in the direction of arrow 23. The string is typically stitched to the end portions 13a and 14a of the strips, as for example is indicated by string upper extents 22a extending across the strip abutting ends indicating by line 24; string lower extents 22b extending across the line 24; and string extents 22c and 22d extending through the strip end portions. Such stitching is firm enough to hold the strips 13 and 14 in end-to-end relation during normal use of the bandage, but loose enough to allow easy pull-out of the string, after grasping exposed end 22e of the string. Attachment 21 is typically characterized by a similar string 27, adapted to be pulled free in a similar manner.

FIG. 5 is the same as FIG. 2, excepting that the end portions 13a' and 14a' of the strips 13 and 14 overlap one another, or other than extending in end-abutting relation. Stitching 30 has zig-zag configuration.

The bandage 10 may take the general form of a conventional bandage, but specifically differing therefrom by the structure described.

I claim:

1. In a disconnectible section bandage, the combination comprising
   (a) a liquid absorbent, soft, pad of material adapted to be placed over a wound,
   (b) a first strip carrying said material,
   (c) second and third strips each carrying an adhesive adapted to be pressed onto skin areas spaced from the wound, and
   (d) primary and secondary releasable attachments respectively interconnecting said second and third strips said first strip widthwise thereof and adapted to be manipulated to free the connection therebetween each, said attachment comprising a string means adapted to be pull-displaced in a direction generally widthwise of the strips, to be removed from said strips, whereby said first strip being free of adhesive is liftable from the wound without restriction imposed by the adhesive.

2. The combination of claim 1 wherein the strips are releasably stitched to said first, second and third strips.

3. The combination of claim 2 wherein each string has a freely projecting, manually graspable end adapted to be pulled, and the stitching extending transversely of the bandage.

4. The combination of claim 1 wherein said bandage is longitudinally elongated, said second and third strips extending longitudinally at opposite ends of the first strip.

5. The combination of claim 1 wherein said first and second strips extend in end-abutting relation at the locus of said primary attachment.

6. The combination of claim 1 wherein said first and second strips extend in end-overlapping relation at the locus of said primary attachment.

7. The method of removing a bandage from a skin area to which it is attached, the bandage comprising
   (a) a liquid absorbent, soft, pad of material adapted to be placed over a wound,
   (b) a first strip carrying said material,
   (c) a second strip carrying an adhesive adapted to be pressed onto one skin area spaced from the wound, and
   (d) a primary releasable attachment interconnecting said first and second strips widthwise thereof and adapted to be manipulated to free the connection therebetween, said primary attachment comprising a string adapted to be pull-displaced in a direction generally widthwise of the strips, to be removed from the strips, said first strip being free of adhesive so as to be liftable from the wound without restriction imposed by the adhesive,
   (e) a third strip carrying an adhesive adapted to be pressed onto another skin area spaced from the wound, and a secondary releasable attachment interconnecting said third and first strips widthwise thereof and adapted to be manipulated to free the connection therebetween, said secondary attachment also comprising a string adapted to be pull-displaced in a direction generally widthwise of the strips to be removed from the strips, said first strip everywhere spaced from said adhesive carried by the second and third strips,
   (f) one of said strings releasably stitched to the first and second strips in a direction generally widthwise thereof, and the other of said strings releasably stitched to the first and third strips in a direction generally widthwise thereof, the strings spaced from said adhesive, that includes
   (i) pulling said strings free of the strips to free said second and third strips from the first strip,
   (ii) then lifting said strips, separately, from the skin area.

* * * * *

UNITED STATES PATENT AND TRADEMARK OFFICE
CERTIFICATE OF CORRECTION

PATENT NO. : 4,526,166
DATED : July 2, 1985
INVENTOR(S) : Arthur L. Silber

It is certified that error appears in the above-identified patent and that said Letters Patent are hereby corrected as shown below:

Column 3, line 12; "strips said first strip widthwise thereof and adapted" should read --strips to said first strip widthwise thereof and adapted--

Column 3, line 20, "2. The combination of claim 1 wherein the strips are" should read --2. The combination on claim 1 wherein the strings are--

Signed and Sealed this

Twenty-ninth Day of October 1985

[SEAL]

Attest:

Attesting Officer

DONALD J. QUIGG

Commissioner of Patents and Trademarks—Designate